United States Patent [19]
Watanabe

[11] Patent Number: 5,785,829
[45] Date of Patent: Jul. 28, 1998

[54] GAS CONCENTRATION SENSOR

[75] Inventor: Tsao Watanabe, Nagoya, Japan

[73] Assignee: Nippondenso Co., Ltd., Kariya, Japan

[21] Appl. No.: 590,176

[22] Filed: Jan. 23, 1996

[30] Foreign Application Priority Data

Jan. 23, 1995 [JP] Japan .................. 7-027460

[51] Int. Cl.⁶ .................................................. G01N 27/407
[52] U.S. Cl. ...................... 204/427; 204/426; 204/428
[58] Field of Search ........................... 204/421–429

[56] References Cited

U.S. PATENT DOCUMENTS

| | | |
|---|---|---|
| 4,116,797 | 9/1978 | Akatsuka . |
| 4,323,440 | 4/1982 | Akatsuka . |
| 4,502,939 | 3/1985 | Holfelder et al. ............ 204/427 |
| 4,765,881 | 8/1988 | Wertheimer et al. ......... 204/427 |
| 4,786,397 | 11/1988 | Barbieri et al. ............. 204/427 |
| 4,883,643 | 11/1989 | Nishio et al. . |

FOREIGN PATENT DOCUMENTS 53-163190  5/1952  Japan .
62-134061  8/1987  Japan .

*Primary Examiner*—T. Tung
*Attorney, Agent, or Firm*—Cushman Darby & Cushman IP Group of Pillsbury Madison & Sutro LLP

[57] ABSTRACT

An oxygen concentration sensor according to the present invention, which can introduce a large amount of air into the atmospheric chamber easily and can sustain stable detecting characteristics for a long time, includes a sensor element having a first end exposed to measured gas and a second end exposed to atmospheric gas, a cover for covering the second end of the sensor element; and a water repellent member disposed in the cover. In the cover, a space is formed to introduce atmospheric gas therethrough to the sensor element. The cover further includes an outer ventilation hole to introduce atmospheric gas into the space. The water repellent member divides the space into an inner space and an outer space between the sensor element and the outer ventilation hole. Each cross-sectional area of air passages in the inner space and the outer space is larger than that of the air passage of the outer ventilation hole.

30 Claims, 16 Drawing Sheets

GAS CONCENTRATION SENSOR

CROSS REFERENCE TO RELATED APPLICATION

This application is based upon and claims priority from Japanese Patent Application No. 7-27460 filed on Jan. 23, 1995, the content of which is incorporated herein by reference.

BACKGROUND OF THE INVENTION

1. Field of the Invention

The present invention relates to an oxygen concentration sensor used for an air/fuel ratio sensor or the like of an automobile engine.

2. Description of Related Art

A conventional oxygen concentration sensor such as a stoichiometric sensor, or the like used for air/fuel ratio control of an automobile engine has following structure (Japanese Utility Model Laid-Open Publication No. 62-134061).

As shown in FIG. 21, the above-described oxygen concentration sensor 8 includes a sensor element inserted into a housing 10 and a cover disposed to cover an upper part of the sensor element. The cover comprises an outer cover exposed to the atmosphere and an inner cover 83 disposed inside the outer cover.

A tubular water repellent filter 11 is disposed between the outer cover and inner cover 83. The outer cover has outer ventilation holes 827, 828 and 829, and inner cover 83 has inner ventilation holes 839.

The outer cover in the above-mentioned oxygen concentration sensor has a dual structure where a first cover 821 is disposed outside and a second cover 822 is disposed inside first cover 821.

First cover 821 has first outer ventilation holes 827 and 828 at two positions of the upper and the lower portions respectively thereof. Second cover 822 has second outer ventilation holes 829 at an intermediate position between first outer ventilation holes 827 and 828.

A first space 825 is formed between first cover 821 and second cover 822. A second space 826 is formed between second cover 822 and water repellent filter 11.

In the above-described oxygen concentration sensor 8, air is introduced from first outer ventilation holes 827 and 828 (shown with big arrows in FIG. 21) through first space 825 and second outer ventilation holes 829 and second space 826, and reaches an outer permeable surface 112 of water repellent filter 11. Then, the air goes into oxygen concentration sensor 8 from inner ventilation holes 839 through water repellent filter 11 and an inner permeable surface 113, and finally flows into the atmospheric chamber inside the sensor element (shown with smaller arrows in FIG. 21).

Thus, oxygen flowing out from the atmospheric chamber to the measured gas chamber according to the volume for detecting the oxygen concentration can be supplied to the atmospheric chamber of the above-described oxygen concentration sensor 8.

Next, another conventional oxygen concentration sensor having a different structure from the above-described oxygen concentration sensor and using a block-shaped water repellent filter is described. (Japanese Utility Model Laid-Open Publication No. 62-1164).

As shown in FIGS. 22 and 23, an oxygen concentration sensor 9 has an air passage 94 between an inner cover 93 and an outer cover 92. An upper end 942 of air passage 94 is structured to be open to a block-shaped water repellent filter 21. A lower end 941 of air passage 94 is opened to the atmosphere. An end of outer cover 92 is bent upwardly to prevent an extraneous materials such as water drops, oil, dust and so forth from going inside lower end 941 of air passage 94.

In oxygen concentration sensor 9, as shown with arrows in FIG. 22, the air introduced from lower end 941 of air passage 94 flows through air passage 94 and reaches a water repellent filter 21 from upper end 942 of air passage 94. Then the air goes inside water repellent filter 21 through an outer permeable surface 920 which contacts with air passage 94 and water repellent filter 21, and flows inside oxygen concentration sensor 9 through an inner permeable surface 930.

It has been highly demanded that environmental protection such as anti-air pollution measures be dealt with. To meet such demands, a high quality oxygen concentration sensor, which assures a longer maintenance-free period and a longer life than a conventional oxygen concentration sensor, is required for air/fuel control of an engine.

Along with such environmental protection measures, fixing position of an oxygen concentration sensor has been varied. For example, oxygen concentration sensors are disposed in not only the engine room but also the exhaust pipe below a vehicle floor in an air/fuel ratio control system employing plural oxygen concentration sensors.

An oxygen concentration sensor highly resistant to extraneous materials like water, oil and dust is requested more than ever before.

Since regulation to restrict poisonous ingredients in the exhaust gas from an engine becomes more strict year by year, in addition to a conventional stoichiometric sensor (an oxygen concentration sensor optimized to detect theoretical air/fuel ratio), an oxygen concentration sensor (an air/fuel ratio sensor) capable of detecting air/fuel ratio in a wide range from a rich to a lean atmosphere is demanded.

Furthermore, an oxygen concentration sensor, which can detect a rich atmosphere in a wider range and detect with higher accuracy to improve fuel efficiency, is also needed.

A rich atmosphere means the atmosphere of exhaust gas emitted while the engine is running where gas mixture of the fuel and the air introduced into the engine is rich in fuel.

On the other hand, a lean atmosphere, contrary to the above-mentioned rich atmosphere, refers to the atmosphere of exhaust gas emitted where gas mixture of the fuel and air introduced into the engine is lean in fuel.

However, oxygen concentration sensors 8 and 9 shown in FIGS. 21–23 may not satisfy the above-described demands and requirements.

That is, in a rich atmosphere, oxygen goes to the atmospheric chamber disposed inside the sensor element and reaches the measured gas chamber after passing through the solid electrolyte. It is necessary to maintain the oxygen concentration in the atmospheric chamber constantly at the same level with the atmosphere by supplying the oxygen flowing out, in order to obtain an oxygen concentration sensors having high detecting accuracy.

In oxygen concentration sensors 8 and 9, the area of the permeable surfaces which serve as a passing inlet or outlet is small, when air passes through water repellent filters 11 and 21. Therefore, it is difficult to introduce a large amount of air at a time In a situation such that a lower oxygen concentration inside the sensor element is kept for a long time, detecting accuracy of the element will be deteriorated. Furthermore, the water repellent filter is likely to be clogged up due to dust, because the area of the air permeable surfaces is small.

Furthermore, air passage 94 of oxygen concentration sensor 9 shown in FIGS. 22 and 23 has a long and narrow tubular shape, so that air passage 94 is likely to be closed by surface tension when liquid having a high surface tension, such as oil, adheres. As a result, air may not be introduced.

SUMMARY OF THE INVENTION

In light of the above-described problems, a purpose of the present invention is to provide an oxygen concentration sensor capable of introducing a large amount of air into the atmospheric chamber easily and maintaining stable detecting characteristics for a long time.

According to the present invention, an oxygen concentration sensor includes a sensor element having a first end exposed to measured gas and a second end exposed to atmospheric gas, a cover for covering the second end of the sensor element; and a water repellent member disposed in the cover.

In the cover, a space is formed to introduce atmospheric gas therethrough to the sensor element. The cover further includes an outer ventilation hole to introduce atmospheric gas into the space.

The water repellent member divides the space into an inner space and an outer space between the sensor element and the outer ventilation hole.

Each cross-sectional area of air passages in the inner space and the outer space is larger than that of the air passage of the outer ventilation hole.

The most remarkable feature in the present invention is that the outer and the inner spaces are provided at both sides of the water repellent filter, and each cross-sectional area of air passage in the outer and the inner spaces is larger than the sectional area of the outer ventilation hole.

The cover may include an outer cover and an inner cover. The outer space is formed by the outer cover and the water repellent filter, and the inner space is formed by the water repellent filter and the inner cover.

It is preferable that each area of outer and inner permeable surfaces of said water repellent member facing the outer and inner spaces is larger than each of the cross-sectional areas of the air passages of the outer and inner ventilation holes.

The outer permeable surface is the surface of the water repellent filter facing the outer space, through which air flows from the outer space.

Similarly, the inner permeable surface is the surface of the water filter facing the inner space.

It is also preferable that each of the outer and the inner spaces be formed in a ring shape facing the water repellent filter.

In this way, the side surfaces of the water repellent filter can entirely function as the inner and outer permeable surfaces, so that a large amount of air can be introduced at a time.

Plural outer ventilation holes are formed on the outer cover. These plural holes should be preferably formed at offset positions in the axial direction, respectively, so that extraneous materials like water, oil, dust or the like entering the outer space can be easily released from the outer ventilation holes provided below. The outer permeable surface of the water repellent filter can be prevented from being clogged up.

It is also preferable that the space is extended and enlarged up to the portion other than the permeable surface of the water repellent filter. Extraneous materials such as water, oil, dust or the like entering through the outer ventilation holes can be trapped in the enlarged space, so that the permeable surface can be prevented from being clogged up due to the extraneous materials.

It is further preferable that the cover has the outer ventilation holes facing the enlarged space, so that the extraneous materials trapped in the enlarged space can be released from the outer ventilation holes.

The above-mentioned oxygen concentration sensor can be used as an air/fuel ratio sensor in air/fuel ratio control as well as a stoichiometric sensor of an automobile engine.

The above-mentioned air/fuel ratio sensor is a type of oxygen concentration sensor to detect oxygen concentration in the measured gas chamber by applying voltage between the inner and the outer electrodes to move the oxygen ions therebetween and by measuring electric current flowing between the electrodes due to the migration of the oxygen ions.

The above-mentioned stoichiometric sensor is a type of oxygen concentration sensor to detect oxygen concentration in the measured gas chamber by migration of the oxygen ions between the outer and the inner electrodes due to rapid decrease of oxygen concentration of the measured gas around the outer electrode in stoichiometric condition (in a theoretical air/fuel ratio condition) and by measuring electromotive force between the electrodes accompanied by the movement of the oxygen ions.

According to the present invention, air is introduced from the outer ventilation holes to flow into the outer space disposed just inside the outer ventilation holes. Then, the air goes into the water repellent filter through the outer permeable surface of the water repellent filter facing the outer space.

The air flows into the inner space via the inner permeable surface from the inside of the water repellent filter, and moves toward the sensor element through the inner ventilation holes. Therefore, the surface of the water repellent filter can be effectively utilized as an air passage.

For this reason, a sufficient amount of air can be surely introduced to the atmospheric chamber without deteriorating the detecting characteristics even in a rich atmosphere.

In the above-mentioned oxygen concentration sensor, the detecting characteristics will not be deteriorated even if extraneous materials adhere to the outer ventilation holes to obstruct the introduction of the air. While adhering extraneous materials are naturally taken away, the air existing in the outer and the inner spaces can go to the sensor element.

Therefore, the detecting characteristics will not be deteriorated and the oxygen concentration sensor can keep stable detecting characteristics for a long time.

As described above, according to the present invention, it is possible to provide an oxygen concentration sensor capable of introducing a large amount of air to the atmospheric chamber easily and maintaining stable detecting characteristics for a long time.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PREFERRED EMBODIMENTS

The preferred embodiments of the present invention are hereinafter described with reference to the accompanying drawings.

An oxygen concentration sensor according to a first embodiment of the present invention is described with reference to FIGS. 1–5.

Figure 1:
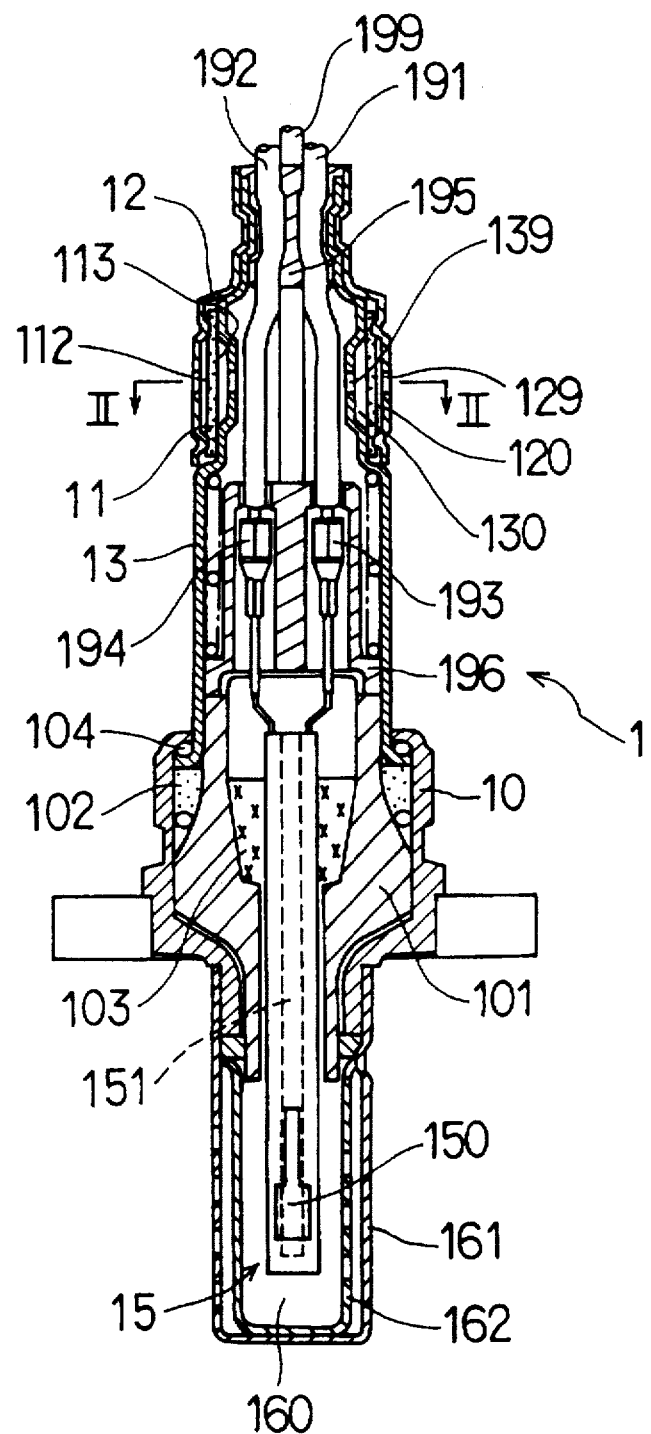
FIG. 1 is a cross-sectional view of an oxygen concentration sensor according to a first embodiment.
Figure 2:
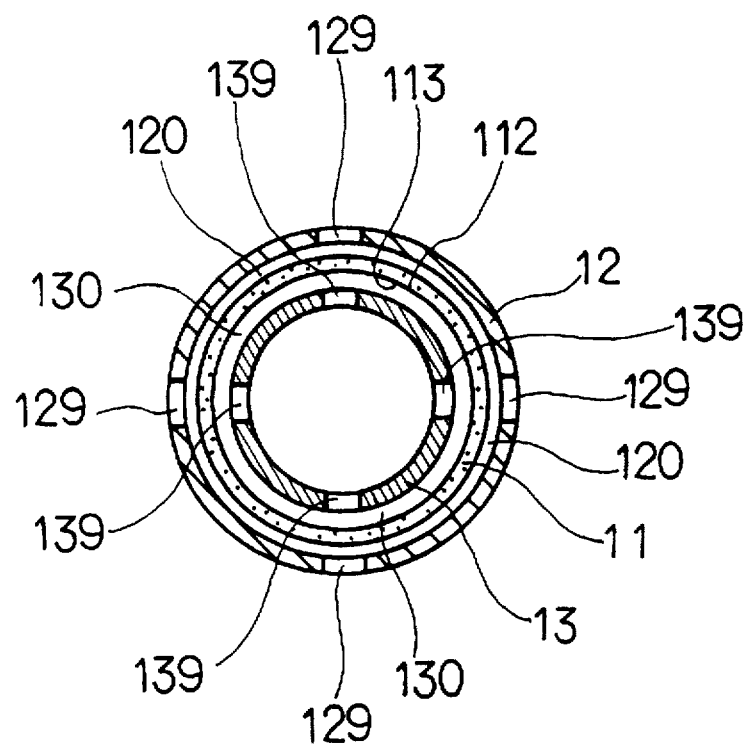
FIG. 2 is a cross-sectional view taken along line II—II of FIG. 1.

As shown in FIGS. 1 and 2, an oxygen concentration sensor 1 of the first embodiment has a sensor element 15 inserted into a housing 10, and a cover disposed to cover the upper part of sensor element 15. The above-mentioned cover comprises an outer cover 12 exposed to the atmosphere and an inner cover 13 disposed inside outer cover 12. A tubular water repellent filter 11 is disposed between outer cover 12 and inner cover 13. Outer cover 12 has outer ventilation holes 129, and inner cover 13 has inner ventilation holes 139.

An outer space 120 facing outer ventilation holes 129 is formed between water repellent filter 11 and outer cover 12. On the other hand, an inner space 130 facing inner ventilation holes 139 is between water repellent filter 11 and inner cover 13.

The area of outer permeable surface 112 of water repellent filter 11 facing outer space 120 is larger than the cross-sectional area of outer ventilation holes 129. Similarly, the area of inner permeable surface 113 of water repellent filter 11 facing inner space 130 is larger than that of inner ventilation holes 139.

As shown in FIG. 2, each of outer space 120 and inner space 130 is formed in a ring shape so as to face water repellent filter 11.

As shown in FIG. 1, double protection covers 161 and 162 forming a measured gas chamber 160 are disposed around the lower end of housing 10 so as to cover the side of sensor element 15.

Inner cover 13 is fixed to the upper part of housing 10 by crimping so as to hold a metal ring 104 therebetween. The lower end of inner cover 13 is in contact with a powdery sealing material 102.

Outer cover 12 is disposed outside inner cover 13. Water repellent filter 11 is disposed between outer cover 12 and inner cover 13, with its top and bottom ends sealed and fixed at the upper and lower portions of outer cover 12.

The above-mentioned sensor element 15 is a laminated type, which comprises a solid electrolyte, an inner electrode disposed in a manner to face atmospheric chamber 151 in the interior of sensor element 15, and an outer electrode 150 disposed in a manner to be exposed to measured gas chamber 160 outside atmospheric chamber 151. Sensor element 15 has a heater integrally.

The outputs from the inner electrode and outer electrode 150 are respectively supplied to lead wires 191 and 192 electrically connected to the outside via each lead terminal 193 and 194. The heater in sensor element 15 is also electrically connected to an outside power source via a lead wire 199.

Sensor element 15 is inserted into housing 10 with a holder 101 therebetween. To keep air-tightness between atmospheric chamber 151 and measured gas chamber 160, powdery sealing material 102 fills the space between housing 10 and a holder 101, and glass sealing material 103 is filled between sensor element 15 and holder 101.

In FIG. 1, numeral 195 denotes a rubber bush, and numeral 196 denotes an insulator.

Next, an operation and effect according to the first embodiment are described.

In oxygen concentration sensor 1 of the first embodiment, the air is introduced from outer ventilation holes 129 and the air is temporarily kept in outer space 120. The air flows into water repellent filter 11 through outer permeable surface 112 of water repellent filter 11 facing outer space 120, and the air goes into inner space 130 through inner permeable surface 113 from the inside of water repellent filter 11. Then, the air finally goes to atmospheric chamber 151 placed in sensor element 15 via inner ventilation holes 139 open to inner space 130.

Therefore, the side of water repellent filter 11 can be effectively used as an air passage. In the oxygen concentration sensor of the present embodiment, the air passage area is prevented from being approximately the same size as the cross-sectional area of the outer ventilation holes by having the water repellent filter come into contact with the outer ventilation holes as was done in the conventional sensors.

Figure 3:
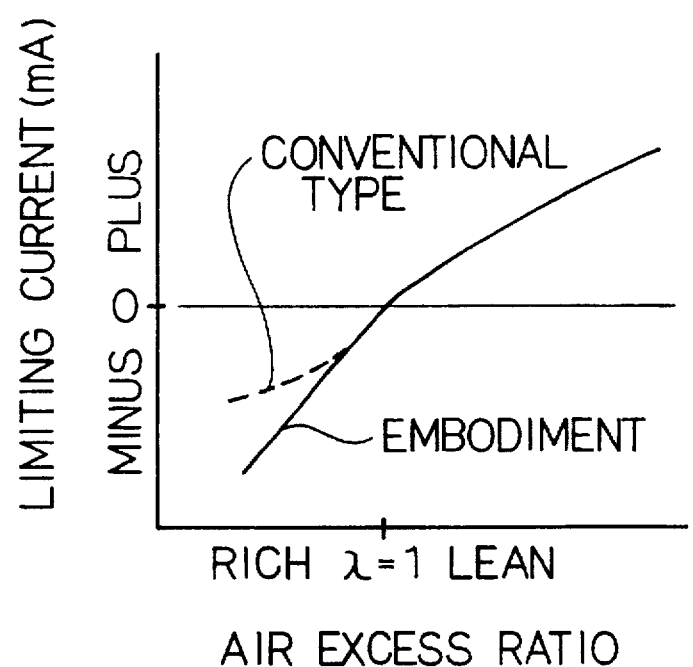
FIG. 3 is a graph showing the relationship between excess air factor and limiting current according to the first embodiment.

Comparing oxygen concentration sensor 1 of this embodiment with the aforementioned conventional oxygen concentration sensor 9, limiting current in sensor 1 varies linearly in accordance with excess air ratio even in a rich atmosphere as shown in FIG. 3.

Figure 22:
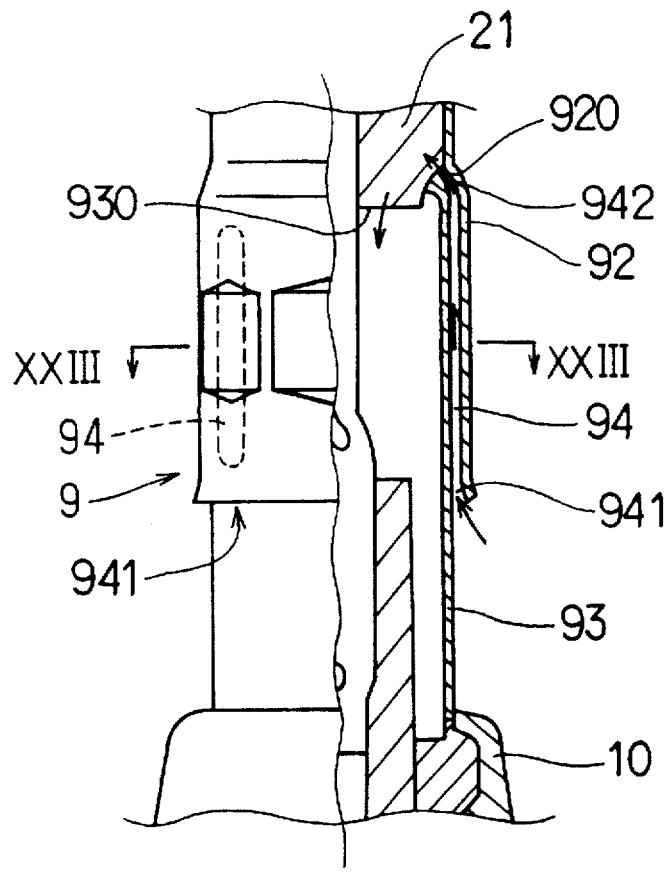
FIG. 22 is a cross-sectional view of main portions of another conventional oxygen concentration sensor.
Figure 23:
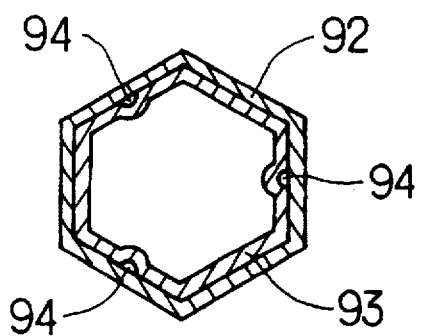
FIG. 23 is a cross-sectional view taken along line XXIII—XXIII of FIG. 22.

In contrast to this embodiment, however, the limiting current of the conventional oxygen concentration sensor 9 shown in FIGS. 22 and 23 does not vary as sharply in accordance with the decrease of excess air ratio in a rich atmosphere. Therefore, the detecting characteristics of the conventional oxygen concentration sensor 9 are deteriorated in a rich atmosphere.

However, oxygen concentration sensor 1 of this embodiment has excellent detecting characteristics even in the rich atmosphere because its structure ensures a sufficient amount of air is introduced to atmospheric chamber 151.

Even though extraneous materials adhere to outer ventilation holes 129 and the introduction of the air may become obstructed in oxygen concentration sensor 1 of this embodiment, the air in inner space 130 and outer space 120 can flow into atmospheric chamber 151, such that the oxygen concentration in atmospheric chamber 151 can be kept to almost the same level as the outside air for a certain period of time while the adhering extraneous materials are naturally taken away.

The following tests have been performed to prove the aforementioned characteristics.

Oil is adhered to the outer ventilation holes 129 of oxygen concentration sensor 1 of this embodiment and the lower portion 941 of the air passage 94 of conventional oxygen concentration sensor 9 shown in FIGS. 22 and 23 to detect respective oxygen concentration in the rich atmosphere.

Figure 4:
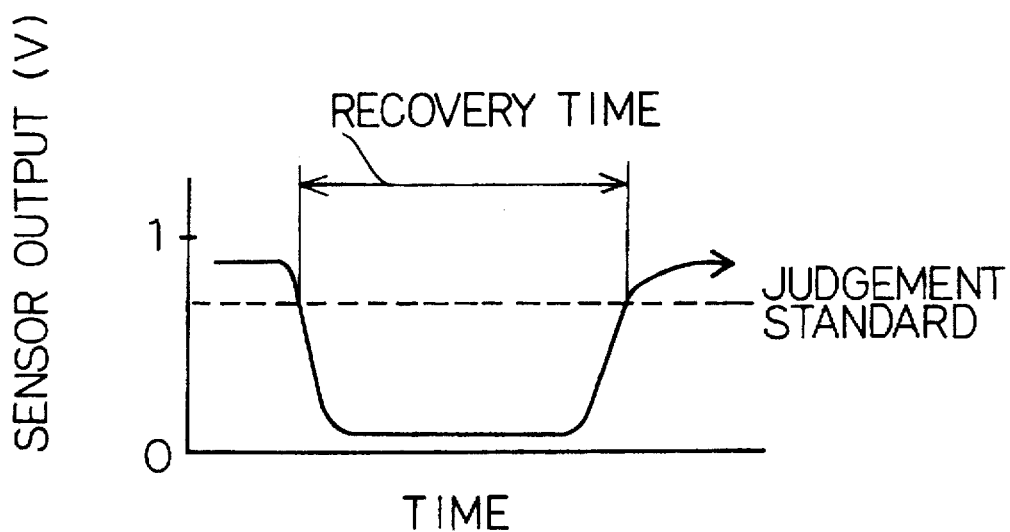
FIG. 4 is a graph representing fluctuation of a sensor output with the lapse of time when oil adheres to the sensor according to the first embodiment.

At that time, atmospheric chamber 151 has an oxygen insufficiency. As shown in FIG. 4, the sensor output, which indicates the detecting characteristics of the oxygen concentration sensors, decreases. As the adhering oil is naturally taken away, however, the sensor output recovers.

Figure 5:
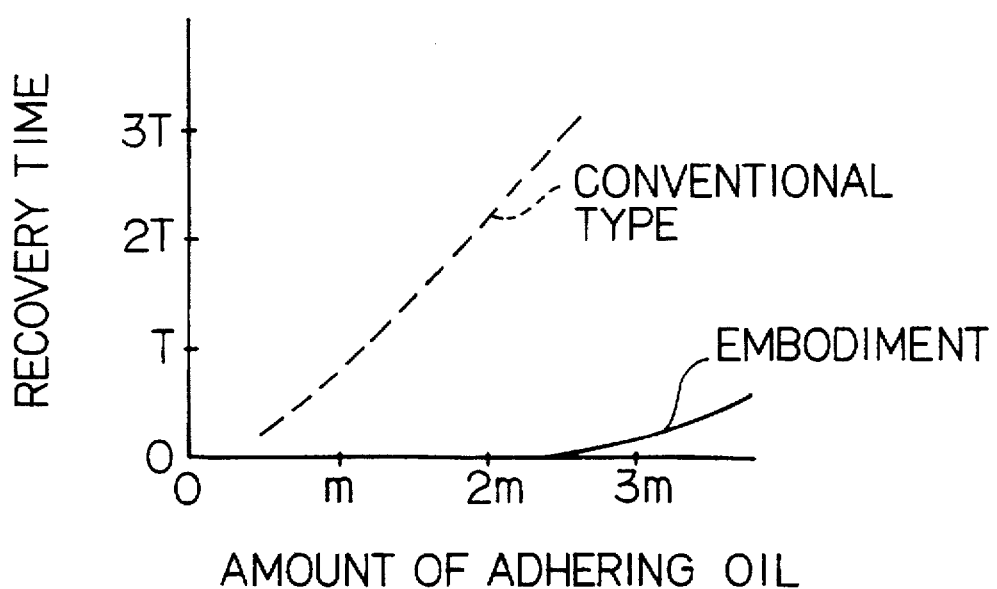
FIG. 5 is a graph representing relationship between the adhering amount of oil and recovery time of the sensor output according to the first embodiment.

The graph in FIG. 5 shows the relationship between the recovery time and the amount of adhering oil. In this graph, the recovery time represents a necessary period of time for the sensor output to recover and satisfy a certain judgement standard, after the output drops below the judgement standard. The horizontal axis (m, 2 m and 3 m) of the graph represents the amount of adhering oil.

As can be seen from FIG. 5, in oxygen concentration sensor 1 of this embodiment, there is almost no decrease of the sensor output due to the adhesion of the oil, and also the output recovers very quickly even after the sensor output decreases. However, in conventional oxygen concentration sensor 9, it is difficult to obtain a quick recovery when the sensor output decreases due to adhesion of the oil.

As described above, it is clear that oxygen concentration sensor 1 of this embodiment can strongly resist extraneous materials adhering to the outer ventilation holes and also maintain stable detecting characteristics for a long time.

Therefore, this embodiment can provide an oxygen concentration sensor capable of introducing a large amount of air into the atmospheric chamber easily and to maintaining stable detecting characteristics for a long time.

Next, modifications of the first embodiment are described. These modifications relate to oxygen concentration sensors having various types of covers as shown in FIGS. 6–10.

Figure 6:
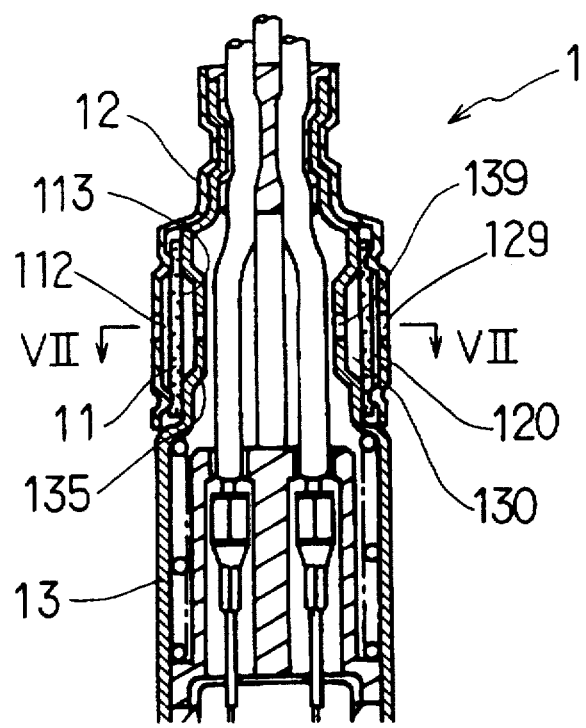
FIG. 6 is a cross-sectional view of main portions of an oxygen concentration sensor according to a modification of the first embodiment.
Figure 7:
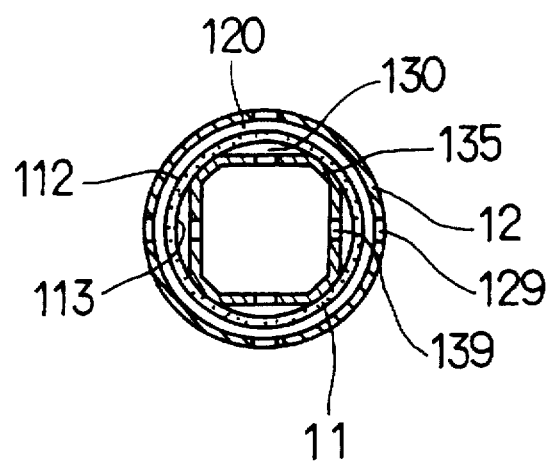
FIG. 7 is a cross-sectional view taken along line VII—VII of FIG. 6.

In an oxygen concentration sensor 1 shown in FIGS. 6 and 7, an outer surface 135 (of an inner cover 13) facing a water repellent filter 11 is prism-shaped. Four outer sides along their ridge lines of a surface 135 have curved surfaces to contact with tubular water repellent filter 11.

The outer surfaces along the ridge lines define four inner smaller spaces 130, each of which corresponds to an inner ventilation hole 139 provided in inner cover 13 facing an inner surface of water repellent filter 11.

The other features are the same as in the first embodiment.

Figure 8:
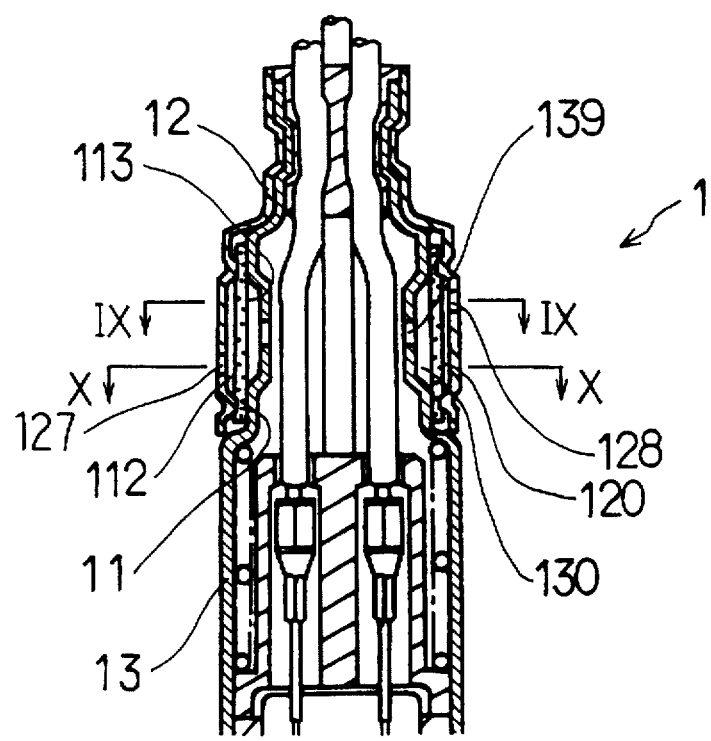
FIG. 8 is a cross-sectional view of main portions of another modification of the oxygen concentration sensor according to the first embodiment.
Figure 9:
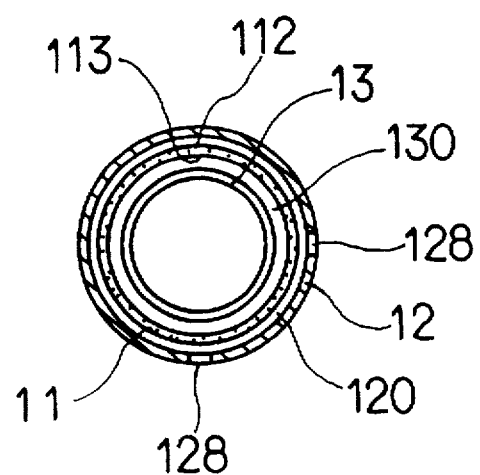
FIG. 9 is a cross-sectional view taken along line IX—IX of FIG. 8.
Figure 10:
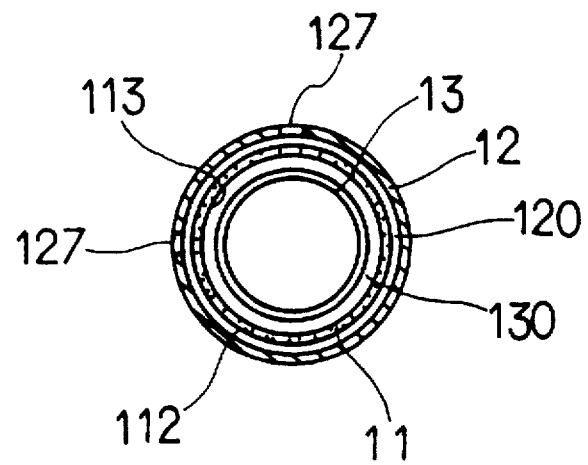
FIG. 10 is a cross-sectional view taken along line X—X of FIG. 8.

In oxygen concentration sensor 1 shown in FIGS. 8–10, a pair of two outer ventilation holes 127 and 128 are disposed at offset positions in its axial direction respectively. That is, in FIG. 8, outer ventilation hole 128 on the right side is disposed above inner ventilation hole 139 while outer ventilation hole 127 on the left side are disposed below inner ventilation hole 139.

The other features are the same as in the first embodiment.

In oxygen concentration sensor 1 shown in FIGS. 6 and 7 of this embodiment, water repellent filter 11 can be fixed much more firmly to outer cover 12, because the contacting area of water repellent filter 11 with surface 135 (of inner cover 13) facing filter 11 is enlarged, .

The other operation and effect are the same as in the first embodiment.

In oxygen concentration sensor 1 shown in FIGS. 8–10, extraneous materials entering outer space 120 can be released from outer ventilation holes disposed below by selecting the fixing position of oxygen concentration sensor 1, so that outer permeable surface 112 of water repellent filter 11 can be prevented from being clogged up due to the extraneous materials.

The other operation and effect are the same as in the first embodiment 2.

Next, a second embodiment of the present invention is described.

Figure 11:
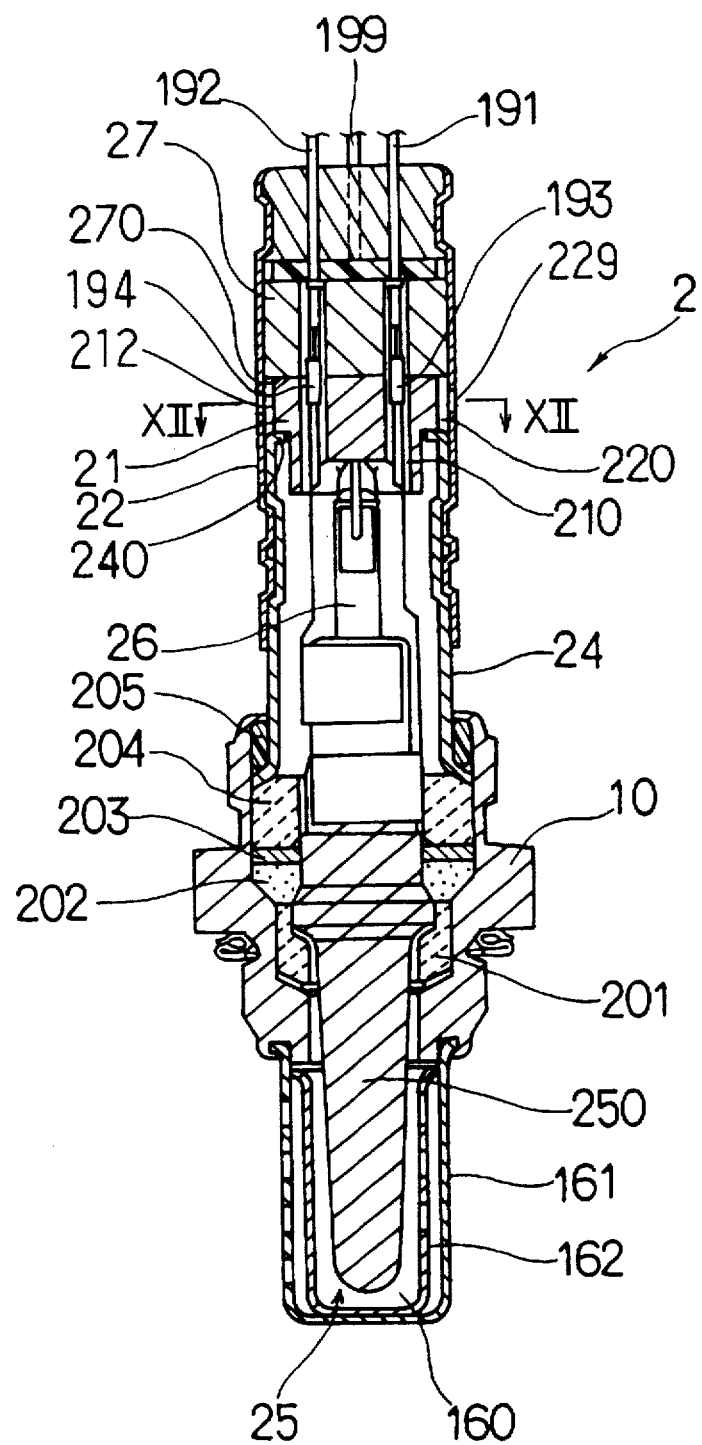
FIG. 11 is a cross-sectional view of an oxygen concentration sensor according to a second embodiment.
Figure 12:
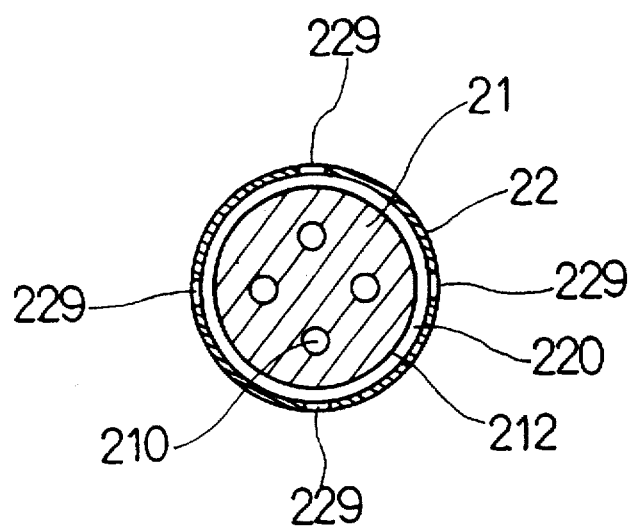
FIG. 12 is a cross-sectional view taken along line XII—XII of FIG. 11.

In the aforementioned first embodiment, tubular-shaped water repellent filters are employed, however, the second embodiment as shown in FIGS. 11 and 12 includes a block-shaped water repellent filter 21 and a cup-shaped sensor element 25.

As shown in FIG. 11, oxygen concentration sensor 2 of this embodiment includes cup-shaped sensor element 25 inserted into a housing 10 and covers 22 and 24 disposed to cover the upper part of sensor element 25.

The above-mentioned cover has outer ventilation holes 229. Block-shaped tubular water repellent filter 21 is disposed in a manner to face outer ventilation holes 229 of outer cover 22.

As shown in FIGS. 11 and 12, outer space 220 facing outer ventilation holes 229 is formed between water repellent filter 21 and outer cover 22. The area of outer permeable surface 212 of water repellent filter 21 facing outer space 220 is larger than the cross-sectional area of outer ventilation holes 229.

As shown in FIG. 12, space 220 is formed in a ring shape so as to face water repellent filter 21.

As shown in FIG. 11, double protection covers 161 and 162 for forming a measured gas chamber 160 are disposed around a lower end of housing 10 to cover the side of sensor element 25.

The lower end of cover 24 is fixed to the upper end of housing 10 by crimping so as to hold a metal ring 205 therebetween. Cover 22 is disposed above cover 24. A block-shaped water repellent filter 21 is sealed in cover 22 so as to be fixed between the upper end 240 of cover 24 and the lower end 270 of an elastic supporter 27.

Sensor element 25 has a cup shape and includes a solid electrolyte in a substantially test tubular shape, an inner electrode disposed in a manner to face the atmospheric chamber in the interior of sensor element 25, and an outer electrode 250 exposed to measured gas chamber 160 in the exterior of the atmospheric chamber. Sensor element 25 has a heater 26 inserted into the atmospheric chamber.

Outer electrode 250 and inner electrode are respectively connected with lead wires 191 and 192 via lead terminals 193 and 194. A heat generating unit, electrically connected to an outside power source via a lead wire 199, is incorporated in heater 26.

As shown in FIG. 12, water repellent filter 21 has four insertion portions 210 to dispose lead terminals 193, 194 or the like.

Sensor element 25 is inserted into housing 10 with an insulator 201 therebetween. To keep air-tightness between the atmospheric chamber and the measured gas chamber, powdery sealing material 202 is filled in the space with insulator 201. Powdery sealing material 202 is pressed by pad 203 and insulator 204.

The other features are the same as in the first embodiment.

Water repellent filter 21 and cover 22 in oxygen concentration sensor 2 according to this embodiment are designed to structurally enable the introduction of a large amount of air.

When detecting oxygen concentration, the detecting accuracy is not deteriorated even in the rich atmosphere where oxygen ions migrate from the atmospheric chamber to the measured gas chamber 160. Oxygen concentration sensor 2 of this embodiment has an excellent performance as a fuel/air ratio sensor used specifically for an automobile engine.

The other operation and effect are the same as in the first embodiment.

A third embodiment is hereinafter described. As shown in FIGS. 13–18, in the third embodiment, oxygen concentration sensors include water repellent filters having various shapes.

Figure 13:
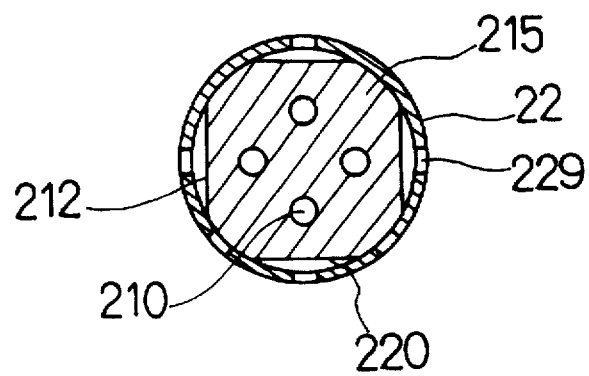
FIG. 13 is a transverse cross-sectional view of an oxygen concentration sensor according to a third embodiment.

In an oxygen concentration sensor shown in FIG. 13, a water repellent filter 215 having a polygonal cross-sectional shape and disposed in a cylindrical cover 22. Water repellent filter 215 has curved surfaces along its ridge lines to contact with the inner wall of cover 22.

The other features are the same as in the first embodiment.

Figure 14:
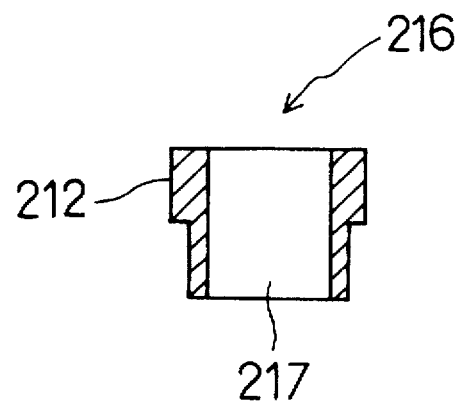
FIG. 14 is a vertical cross-sectional view of a water repellent filter according to the third embodiment.
Figure 15:
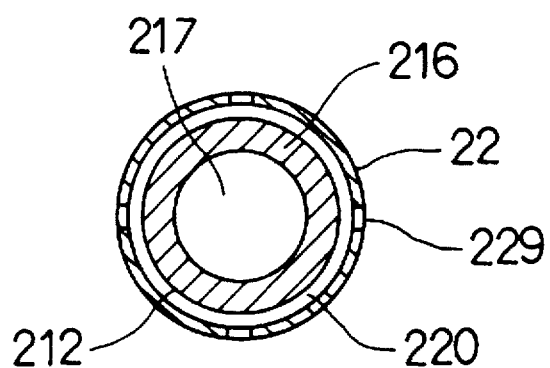
FIG. 15 is a transverse cross-sectional view of a modification of the oxygen concentration sensor according to the third embodiment.

A water repellent filter 216 of an oxygen concentration sensor shown in FIGS. 14 and 15 has a space 217 into which lead terminals and so on are inserted. The lead terminals electrically connect the sensor element and the heater to the outside.

The other features are the same as in the first embodiment.

Figure 16:
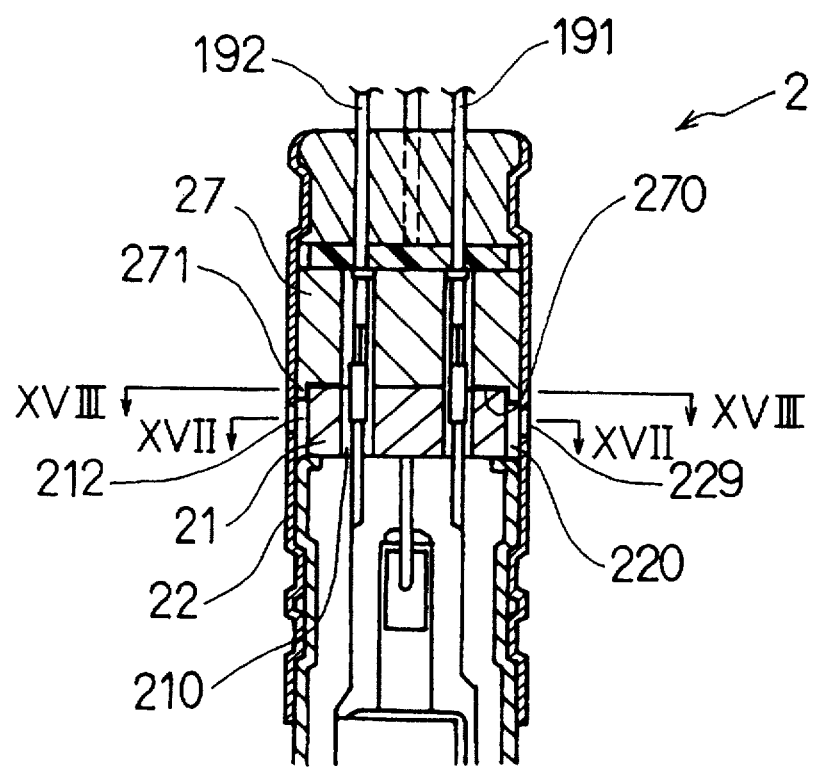
FIG. 16 is a cross-sectional view of main portions of another modification of the oxygen concentration sensor according to the third embodiments
Figure 17:
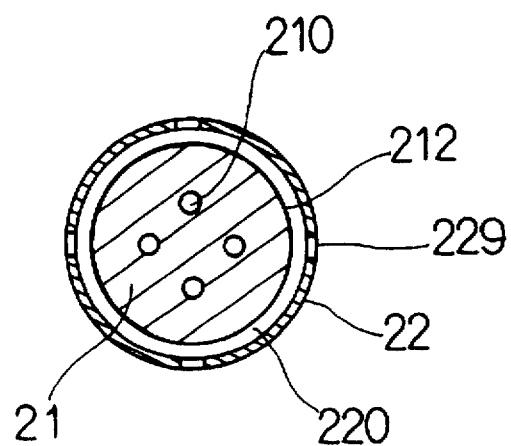
FIG. 17 is a cross-sectional view taken along line XVII—XVII of FIG. 16.
Figure 18:
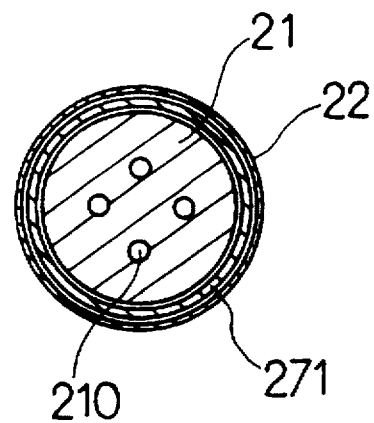
FIG. 18 is a cross-sectional view taken along line XVIII—XVIII of FIG. 16.

In an oxygen concentration sensor 2 shown in FIGS. 16–18, the outer periphery 271 of the bottom 270 of the elastic supporter 27 extends in its axial direction to seal a water repellent filter 21, the radial position of filter 21 being thereby fixed.

The other features are the same as in the first embodiment.

The area of water repellent filter 21 coming into contact with cover 22 is enlarged in oxygen concentration sensor 2 shown in FIG. 13 of this embodiment in the same manner as the oxygen concentration sensors in FIGS. 6 and 7, so that water repellent filter 21 can be firmly fixed.

The other operations and effects are the same as in the first embodiment.

Since the thickness of water repellent filter 21 of oxygen concentration sensors shown in FIGS. 14 and 15 is thin, the air can pass through water repellent filter 21 much more easily.

The other operations and effects are the same as in the first embodiment.

Furthermore, when a position for water repellent filter 21 is fixed at a predetermined position in oxygen concentration sensor 2 in FIGS. 16–18, standard positioning is set based on elastic supporter 27. Therefore, it is not necessary to provide a stepped surface or the like as for standard positioning for the water repellent filter 21, which consequently makes it easier to manufacture the water repellent filter 21.

The other operations and effects are the same as in the first embodiment.

Next, a fourth embodiment of the present invention is hereinafter described.

Figure 19:
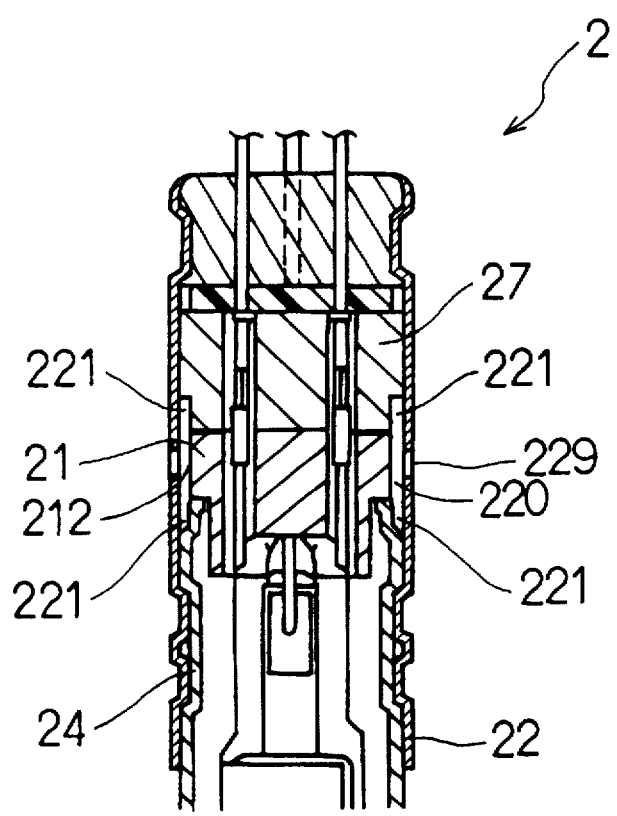
FIG. 19 is a cross-sectional view of main portions of an oxygen concentration sensor according to a fourth embodiment.
Figure 20:
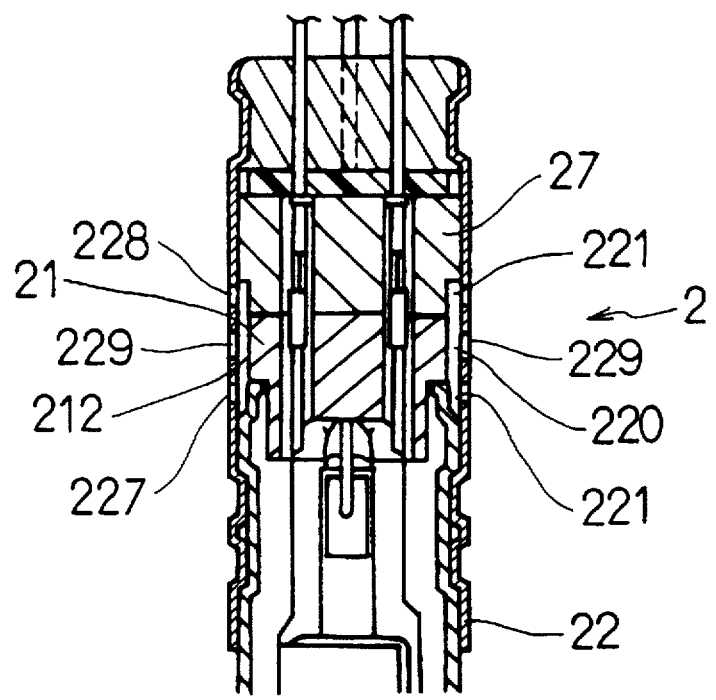
FIG. 20 is a cross-sectional view of main portions of a modification of the oxygen concentration sensor according to the fourth embodiment.
Figure 21:
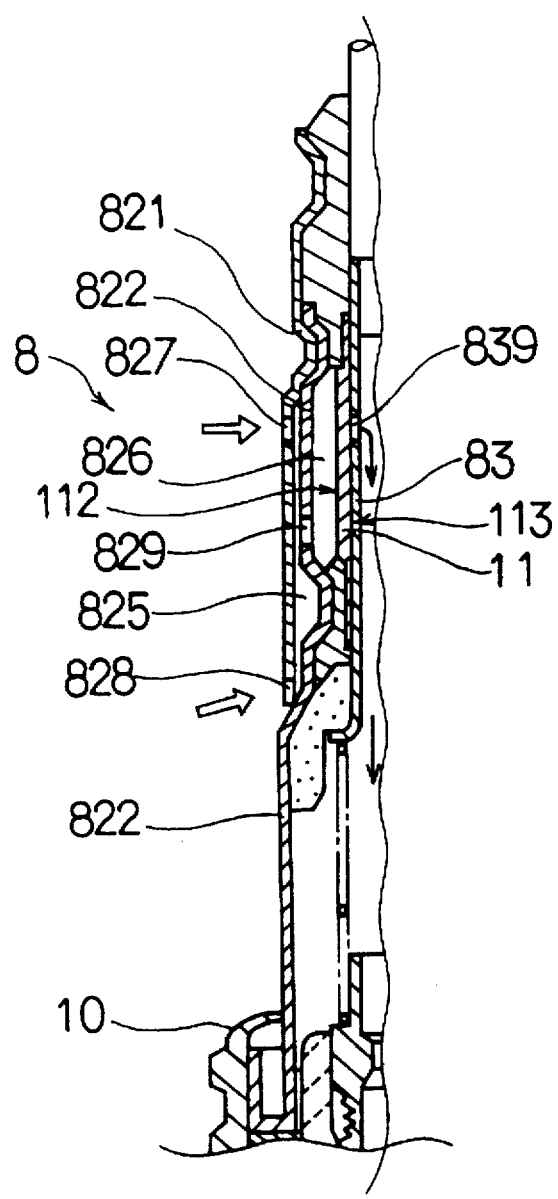
FIG. 21 is a cross-sectional view of main portions of a conventional oxygen concentration sensor.

As shown in FIGS. 19 and 20, oxygen concentration sensor 2 has a space which is enlarged (an enlarged space 221) to cover some portions in addition to permeable surface 212 on water repellent filter 21.

Oxygen concentration sensor 2 shown in FIG. 19 has a space 220 defined by water repellent filter 21 and cover 22. An enlarged upper space 221 is formed on the top of space 220 by elastic supporter 27 and cover 22. An enlarged bottom space 221 is also formed on the bottom of space 220 by covers 24 and 22.

The other features are the same as in the first embodiment.

Cover 22 of oxygen concentration sensor 2 shown in FIG. 20 has outer ventilation holes 227 and 228 facing the aforementioned enlarged space 221.

The other features are the same as in the first embodiment.

Oxygen concentration sensor 2 shown in FIG. 19 of the present embodiment can trap extraneous materials entering from outer ventilation holes 229 in enlarged space 221, so that permeable surface 212 is prevented from being clogged up.

The other operations and effects are the same as in the first embodiment.

Meanwhile, in oxygen concentration sensor 2 shown in FIG. 20 of this embodiment, extraneous materials trapped in enlarged space 221 can be released from outer ventilation holes 227 provided below.

The other operations and effects are the same as in the first embodiment.

The present invention should not be limited to the above-described embodiments but may be modified in many other ways without departing from the spirit of the invention.

What is claimed is:

1. A gas concentration sensor comprising:
   a housing;
   a sensor element inserted into said housing and having a first end exposed to measured gas and a second end exposed to atmospheric gas;
   a cover for covering said second end of said sensor element and having a space formed therein, through which said atmospheric gas is introduced to said sensor element, said cover including:
  an outer ventilation hole formed at a side surface of said cover, for introducing said atmospheric gas into said sensor element, and
  an inner ventilation hole formed at a side surface of said cover radially inwardly of said outer ventilation hole, for introducing said atmospheric gas into said sensor element; and
  a water repellent member disposed in said space radially between said outer ventilation hole and said inner ventilation hole, said water repellent member having axial ends and dividing said space into an inner space and an outer space,
  wherein an area of an outer permeable surface of said water repellent member is larger than an outer total passage area of said outer ventilation hole,
  an area of an inner permeable surface of said water repellent member is larger than an inner total passage area of said inner ventilation hole; and
  said water repellent member contacts said cover only at said axial ends.

2. A gas concentration sensor according to claim 1, wherein,
  said cover includes:
    an outer cover exposed to an atmosphere and having said outer ventilation hole, and
    an inner cover disposed inside said outer cover and having said inner ventilation hole;
  said water repellent member is disposed between said outer cover and said inner cover in such a manner that said outer space is enclosed by at least said outer cover and said water repellent member and that said inner space is enclosed by at least said inner cover and said water repellent member; and
  said outer cover contacts said water repellent member only at a radially outer surface of said axial ends and said inner cover contacts said water repellent member only at a radially inner surface of said axial ends.

3. A gas concentration sensor according to claim 2, wherein each said area of said outer permeable surface and said inter permeable surface of said water repellent member facing said outer space and said inner space is larger than each total passage area, through which air passes, of said outer ventilation hole and said inner ventilation hole.

4. A gas concentration sensor according to claim 2, wherein said inner space is formed in a substantially cylindrical shape facing said water repellent member.

5. A gas concentration sensor according to claim 2, wherein;
  plural pairs of adjacent outer ventilation holes are formed on said outer cover, each pair of adjacent outer ventilation holes are disposed at different positions in an axial direction.

6. A gas concentration sensor according to claim 2, wherein four outer sides of an inner surface of said inner cover have curved surfaces contacting said water repellent member.

7. A gas concentration sensor according to claim 1, wherein said outer space is formed in a substantially cylindrical shape facing said water repellent member.

8. A gas concentration sensor according to claim 1, wherein,
  said cover includes:
    an outer cover exposed to an atmosphere and having said outer ventilation hole, and
    an inner cover disposed inside said outer cover and having said inner ventilation hole to introduce said atmospheric gas into said sensor element;
  said water repellent member is disposed between said outer cover and said inner cover in such a manner that said inner space is enclosed by at least said inner cover and said water repellent member and that said outer space is enclosed by at least said outer cover, said water repellent member and said inner cover; and
  said outer cover contacts said water repellent member only at a radially outer surface of said axial ends and said inner cover contacts said water repellent member only at a radially inner surface of said axial ends.

9. A gas concentration sensor according to claim 8, wherein said outer cover has said outer ventilation hole at a portion facing said inner cover.

10. A gas concentration sensor according to claim 8, wherein said sensor element is cup-shaped and said water repellent member is block-shaped.

11. A gas concentration sensor according to claim 1, wherein said sensor element is laminated and said water repellent member is cylindrical.

12. A gas concentration sensor according to claim 1, wherein said gas concentration sensor is an air/fuel ratio sensor.

13. A gas concentration sensor according to claim 1, wherein,
  said water repellent member is formed in a cylindrical shape,
  said cover includes an outer cover and an inner cover disposed inside said outer cover, said water repellent member being disposed between said outer cover and said inner cover,
  each of said outer cover and said inner cover has a ventilation hole at a side surface thereof; and
  said outer cover contacts said water repellent member only at a radially outer surface of said axial ends and said inner cover contacts said water repellent member only at a radially inner surface of said axial ends.

14. A gas concentration sensor according to claim 1, wherein said water repellent member is fixed in place due to contacting said cover only at said axial ends.

15. A gas concentration sensor comprising:
  a housing;
  a sensor element inserted into said housing and having a first end exposed to measured gas and a second end exposed to atmospheric gas;
  an inner cover for covering said second end of said sensor element;
  an outer cover disposed outside said inner cover to form a space therebetween;
  a water repellent member disposed between said inner cover and said outer cover,
  wherein,
  each of said inner cover and said outer cover has a plurality of ventilation holes on a side surface thereof in a region so as to face said water repellent member, which are formed at different peripheral positions from each other,
  a surface area of said water repellent member at an outer side, through which gas passes, is larger than a total passage area of said ventilation holes formed on said outer cover,
  a surface area of said water repellent member at an inner side, through which gas passes, is larger than a total passage area of said ventilation holes formed on said inner cover, said water repellent member and said outer cover collectively define an outer space therebetween, said outer space having an area larger than said total passage area of said ventilation holes formed on said outer cover; and said water repellent member and said inner cover collectively define an inner space therebetween, said inner space having an area larger than said total passage area of said ventilation holes formed on said inner cover.

16. A gas concentration sensor according to claim 15, wherein, said water repellent member is disposed between said outer cover and said inner cover in such a manner that said outer space is enclosed by at least said outer cover and said water repellent member and that said inner space is enclosed by at least said inner cover and said water repellent member.

17. A gas concentration sensor according to claim 16, wherein said inner space is formed in a substantially cylindrical shape facing said water repellent member.

18. A gas concentration sensor according to claim 16, wherein plural pairs of adjacent outer ventilation holes are formed on said outer cover, each pair of adjacent outer ventilation holes being disposed at different positions in an axial direction.

19. A gas concentration sensor according to claim 16, wherein four outer sides of an inner surface of said inner cover have curved surfaces contacting said water repellent member.

20. A gas concentration sensor according to claim 15, wherein said outer space is formed in a substantially cylindrical shape facing said water repellent member.

21. A gas concentration sensor according to claim 15, wherein, said water repellent member is disposed between said outer cover and said inner cover in such a manner that said inner space is enclosed by at least said inner cover and said water repellent member and that said outer space is enclosed by at least said outer cover, said water repellent member and said inner cover.

22. A gas concentration sensor according to claim 21, wherein said outer cover has said outer ventilation holes at a portion facing said inner cover.

23. A gas concentration sensor according to claim 21, wherein said sensor element is cup-shaped and said water repellent member is block-shaped.

24. A gas concentration sensor according to claim 15, wherein said sensor element is laminated and said water repellent member is cylindrical.

25. A gas concentration sensor according to claim 15, wherein said gas concentration sensor is an air/fuel ratio sensor.

26. A gas concentration sensor according to claim 15, wherein said water repellent member is formed in a cylindrical shape.

27. A gas concentration sensor according to claim 15, wherein said inner cover is tubular.

28. A gas concentration sensor according to claim 15, wherein said outer cover is tubular.

29. A gas concentration sensor according to claim 15, wherein said water repellent member is tubular.

30. A gas concentration sensor according to claim 15, wherein each of said inner cover, said outer cover and said water repellent member is tubular.

* * * * *

UNITED STATES PATENT AND TRADEMARK OFFICE
CERTIFICATE OF CORRECTION

PATENT NO. : 5,785,829
DATED : July 28, 1998
INVENTOR(S) : Watanabe

It is certified that error appears in the above-identified patent and that said Letters Patent is hereby corrected as shown below:

On the title page: Item [75]Inventors: should be --Isao Watanabe--.

Signed and Sealed this

Fifth Day of January, 1999

Attest:

Attesting Officer

*Acting Commissioner of Patents and Trademarks*